United States Patent [19]
Kortenbach

[11] Patent Number: 5,707,392
[45] Date of Patent: Jan. 13, 1998

[54] HERMAPHRODITIC STAMPED FORCEPS JAW FOR DISPOSABLE ENDOSCOPIC BIOPSY FORCEPS AND METHOD OF MAKING THE SAME

[75] Inventor: Juergen Andrew Kortenbach, Miami Springs, Fla.

[73] Assignee: Symbiosis Corporation, Miami, Fla.

[21] Appl. No.: 536,055

[22] Filed: Sep. 29, 1995

[51] Int. Cl.$^6$ .................................................. A61B 10/00
[52] U.S. Cl. ........................................ 606/207; 128/751
[58] Field of Search ............................ 606/51, 52, 170, 606/174, 205–210; 128/750–755

[56] References Cited

U.S. PATENT DOCUMENTS

| | | |
|---|---|---|
| 4,971,067 | 11/1990 | Bolduc et al. . |
| 5,172,700 | 12/1992 | Bencini et al. . |
| 5,267,998 | 12/1993 | Hagen . |
| 5,383,471 | 1/1995 | Funnell ................................ 606/170 |
| 5,471,992 | 12/1995 | Banik et al. ............................ 606/170 |

*Primary Examiner*—William Lewis
*Attorney, Agent, or Firm*—Finnegan, Henderson, Farabow, Garrett and Dunner, L.L.P.

[57] ABSTRACT

Hermaphroditic biopsy forceps jaws for use in an endoscopic biopsy forceps instrument are made from a flat sheet of stainless steel or other suitable material which is stamped and then progressively formed into a jaw cup having a tang. According to the presently preferred embodiment of the invention, the jaw is provided with two substantially parallel tangs, one being shorter than the other. Both tangs are provided with central mounting holes for mounting the jaw on an axle pin between the arms of a clevis. The longer of the tangs is provided with a hole for coupling it to the distal end of a control wire. The tangs are located such that when the jaws are mounted in the clevis, the short tang of each jaw resides between the two tangs of the other jaw. The stamped jaw of the invention may be provided with or without teeth. The location of the tangs permits the mounting of a knife between the jaws, if desired. Other end effectors of similar construction are also disclosed.

20 Claims, 5 Drawing Sheets

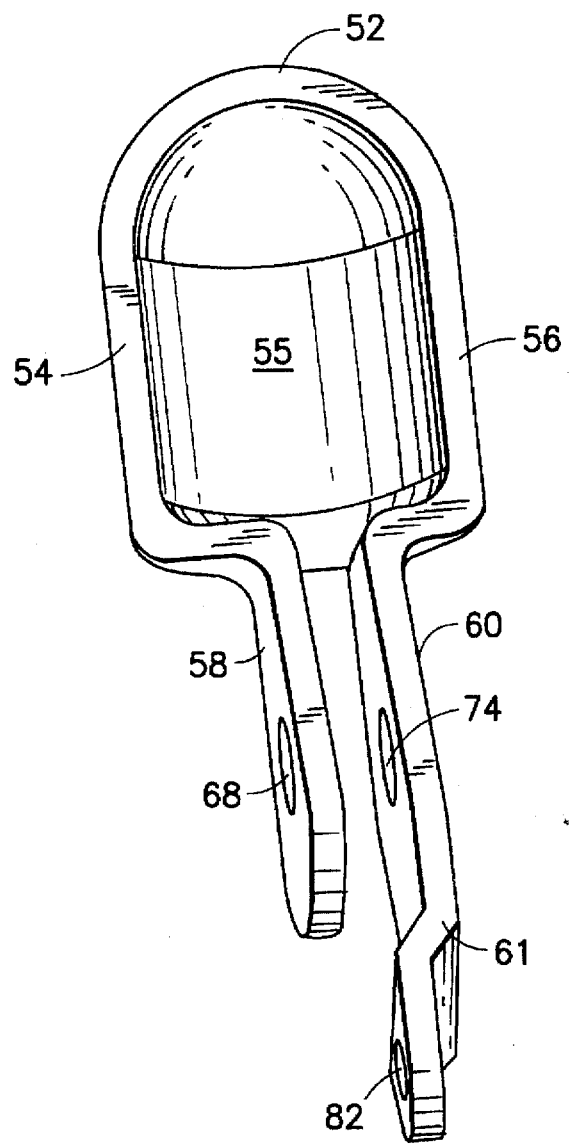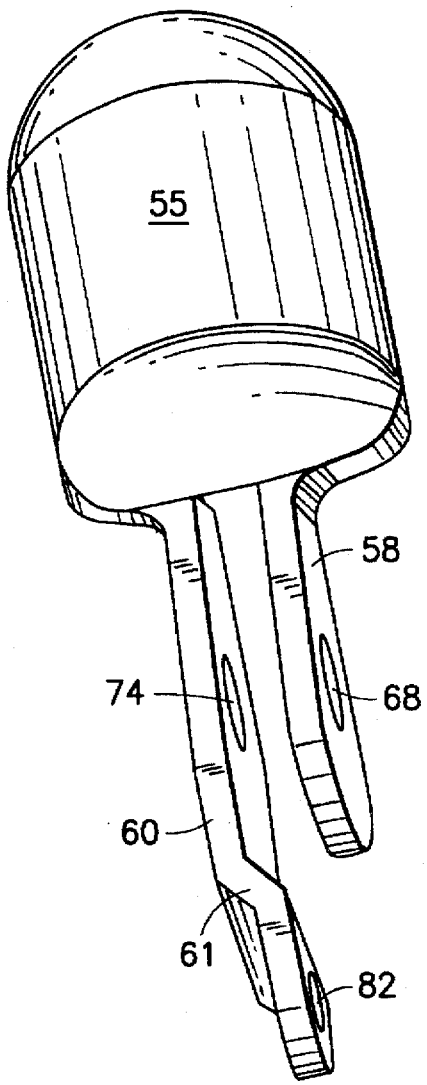
FIG. 8
FIG. 9

HERMAPHRODITIC STAMPED FORCEPS JAW FOR DISPOSABLE ENDOSCOPIC BIOPSY FORCEPS AND METHOD OF MAKING THE SAME

BACKGROUND OF THE INVENTION

1. Field of the Invention

The invention relates to endoscopic instruments. More particularly, the invention relates to biopsy forceps jaws and other endoscopic end effectors which are stamped from a sheet material and progressively formed. For purposes herein, the term "endoscopic" is to be understood in its broad sense to include laparoscopic, arthroscopic, and other microsurgical instruments whether or not used with an endoscope.

2. State of the Art

Endoscopic biopsy forceps are medical instruments which are used in conjunction with an endoscope for taking tissue samples from the human body for analysis. These instruments typically include a long (e.g. 8 foot) slender (e.g. several millimeters in diameter) flexible coil, one or more control wires extending through the coil, a proximal actuating handle coupled to the coil and control wire(s), and a biopsy jaw assembly coupled to the distal ends of the coil and control wire(s). The actuating handle typically moves the control wire(s) relative to the coil to effect a tissue sampling operation by causing the jaws to open and close to bite a tissue sample. A known biopsy forceps instrument is shown in prior art FIGS. 1–4.

As seen in FIGS. 1–4, a known endoscopic biopsy forceps instrument 10 generally includes a proximal handle 12 and a distal end effector assembly 14. A long flexible coil 16 having a pair of axially displaceable control wires 18, 19 extending therethrough couples the handle 12 and the end effector assembly 14. The coil 16 is preferably covered with a PTFE, FEP or polyolefin sheath 15 along substantially all of its length, and a strain relief sleeve 17 may be provided to cover a proximal portion of the coil which extends from the handle 12. The control wires 18, 19 are preferably flexible but longitudinally inelastic and are ideally formed from 304 steel.

The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a coupling means 32 for attaching the proximal ends of the control wires 18, 19.

The end effector assembly 14 includes a clevis 34 which is coupled to the distal end of the coil 16, and a pair of forceps jaws 36, 38. The clevis 34 has a pair of clevis arms 34a, 34b between which the jaws 36, 38 are rotatably mounted on an axle pin 40. Each jaw 36, 38 is provided with a distal cutting edge 36a, 38a, a proximal tang 36b, 38b, and a mounting hole 36c, 38c therebetween. The proximal tangs 36b, 38b are each coupled to the distal end of a respective control wire 18, 19 by means of holes 36d, 38d in the respective tangs. From the foregoing, those skilled in the art will appreciate that relative movement of the shaft 20 and spool 22 results in movement of the control wires 18, 19 relative to the coil 16. Such action results in opening and closing of the jaws 36, 38.

As seen best in FIG. 3, the tang of each jaw is offset from the centerline CL of the jaw cup, thereby permitting the jaw 36 to be substantially identical to jaw 38. Since the jaws 36 and 38 are substantially identical and mating, they are essentially "hermaphroditic".

There are several known variations of the biopsy forceps 10. For example, the jaws 36', 38' may be provided with teeth 36'a, 38'a along their cutting edge; and a flat cutting knife 35 may be provided between the jaws in order to facilitate capture and retention of a biopsy sample.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. While viewing the biopsy site through the optical lens of the endoscope, the practitioner manipulates the actuating handle to effect a tissue sampling operation at the distal end of the instrument. After a sample has been obtained, the practitioner and/or an assistant carefully withdraws the instrument from the endoscope while holding the actuating handle to maintain the jaws in a closed position.

It is understood that in order to be effective in obtaining a biopsy sample, the cutting edge of the forceps jaws should be very sharp. However, due to the small size of the jaws, it is very difficult to make the jaws sharp and durable. Thus far, the best known ways of manufacturing biopsy forceps jaws having sufficient strength and sharpness are by machining a material such as stainless steel into a desired configuration, or by investment casting of bronze or a similar castable material into a desired configuration. While these methods are effective, they are relatively expensive and complex.

SUMMARY OF THE INVENTION

It is therefore an object of the invention to provide an inexpensive method of making an end effector for an endoscopic instrument.

It is also an object of the invention to provide a relatively simple and inexpensive method of making endoscopic biopsy forceps jaws.

It is another object of the invention to provide durable endoscopic end effectors.

It is a further object of the invention to provide endoscopic biopsy forceps jaws which are durable and sharp.

In accord with these objects which will be discussed in detail below, the end effectors of the present invention are made from a flat sheet of stainless steel or other suitable material which is stamped and then progressively formed into an end effector shape with a proximal tang. According to the presently preferred embodiment of the invention, two substantially parallel tangs are formed with one being shorter than the other. Both tangs are provided with central mounting holes for mounting the end effector on an axle pin between the arms of a clevis. The longer of the tangs is provided with a hole for coupling it to the distal end of a control wire. The tangs are located such that when the end effectors are mounted in the clevis, the short tang of each end effector resides between the two tangs of the other end effector.

According to preferred aspects of the invention, the stamped end effector is a biopsy forceps jaw which may be provided with or without teeth. Moreover, the location of the tangs permits the mounting of a knife between the jaws, if desired.

Additional objects and advantages of the invention will become apparent to those skilled in the art upon reference to the detailed description taken in conjunction with the provided figures.

BRIEF DESCRIPTION OF THE DRAWINGS

FIGS. 7 and 8 are perspective views of the innerside of a forceps jaw according to the invention subsequent to the progressive forming of a jaw cup;

FIG. 9 is a perspective view of the outerside of a forceps jaw according to the invention subsequent to the progressive forming of a jaw cup;

DETAILED DESCRIPTION OF THE PREFERRED EMBODIMENTS

Figure 5:
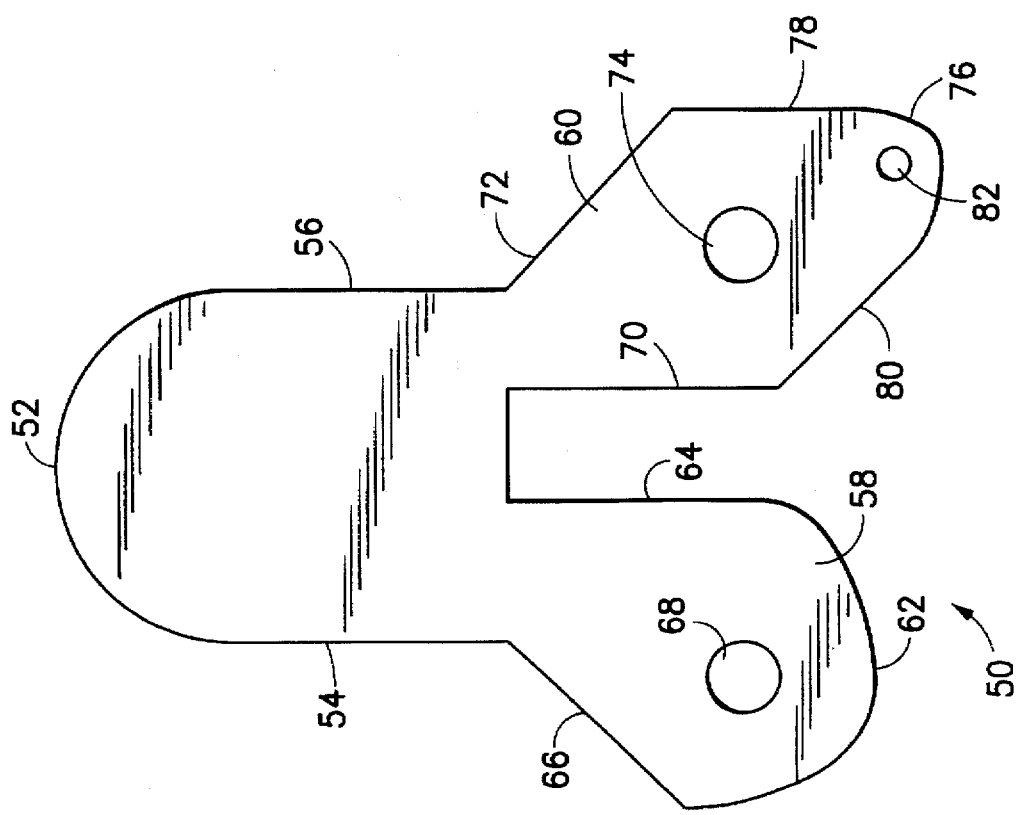
FIG. 5 is a plan view of a stamped forceps jaw according to the invention prior to the progressive forming of a jaw cup.

Turning now to FIG. 5, a biopsy forceps jaw (51 in FIG. 7) according to the invention is made from a flat sheet 50 of stainless steel or other suitable material which is stamped as shown in FIG. 5. The pattern of the stamped sheet 50 has a distal rounded edge 52, two substantially parallel side edges 54, 56 which extend proximally from the rounded distal edge 52, and a pair of proximal lobes 58, 60 which extend proximally and outward from the side edges 54, 56. The first lobe 58 has a curved proximal edge 62, an inner side edge 64 which extends distally and substantially parallel to the side edges 54, 56, and an outer side edge 66 which extends outward at an angle relative to the side edge 54. An axle mounting hole 68 is centrally located on the lobe 58. The second lobe 60 is similar in part to the first lobe 58, having a similar parallel inner side edge 70, a similar angled outer side edge 72, and a similarly located mounting hole 74. The lobe 60 differs from the lobe 58 in that it has a proximal curved edge 76 which is located more distant proximally and outward as compared to the proximal curved edge 62 of the lobe 58. The proximal curved edge 76 is joined to the side edges 70, 72 by an outer parallel side edge 78 and an inner angled side edge 80. As will be described in detail below, the stamped sheet 50 is progressively formed to create a jaw cup with two tangs. The cutting edge of the jaw cup will be formed from the edges 52, 54, 56. Consequently these edges may be sharpened prior to progressive forming.

Figure 1:
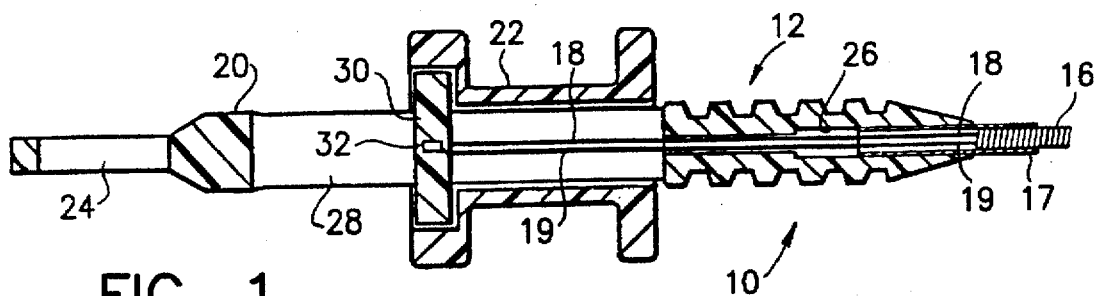
FIG. 1 is a broken side elevation view in partial section of the proximal end of a prior art endoscopic biopsy forceps instrument.
Figure 2:
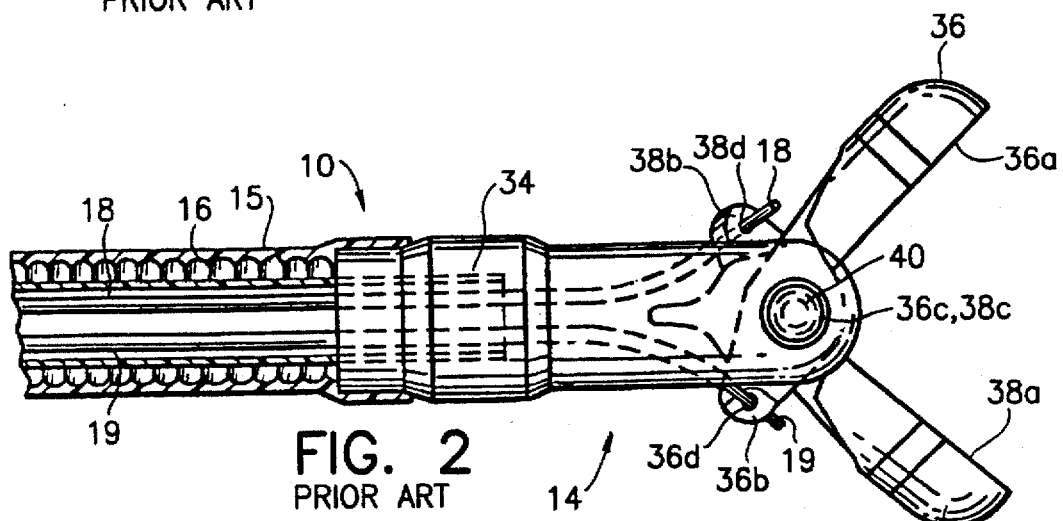
FIG. 2 is an enlarged broken side elevation view in partial section of the distal end of a prior art endoscopic biopsy forceps instrument.
Figure 3:
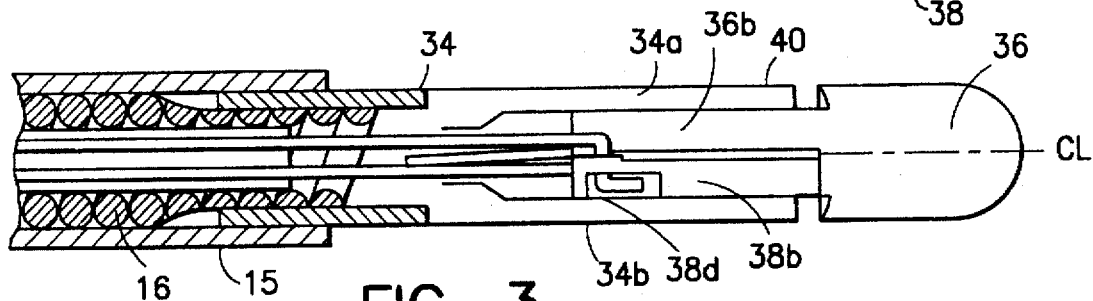
FIG. 3 is an enlarged broken top view in partial section of the distal end of a prior art endoscopic biopsy forceps instrument.
Figure 4:
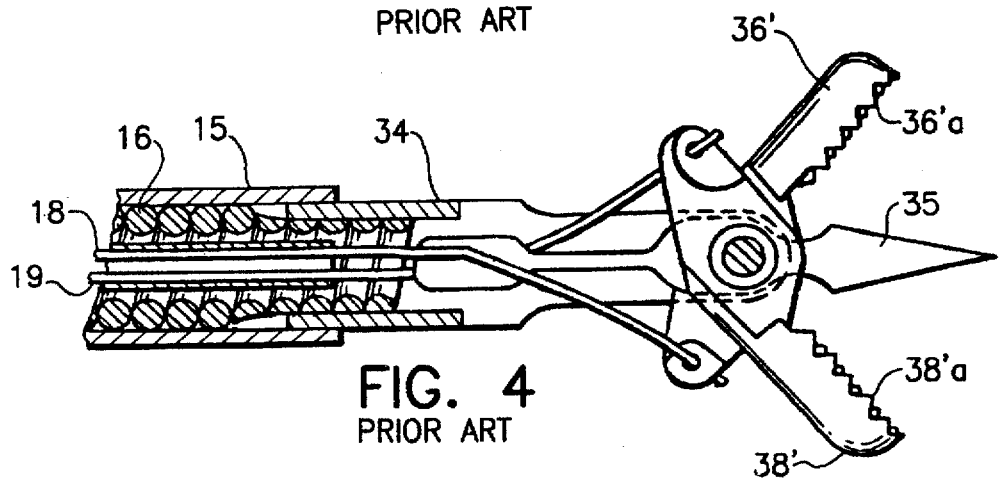
FIG. 4 is a view similar to FIG. 2 of another embodiment of a prior art biopsy forceps instrument.
Figure 6:
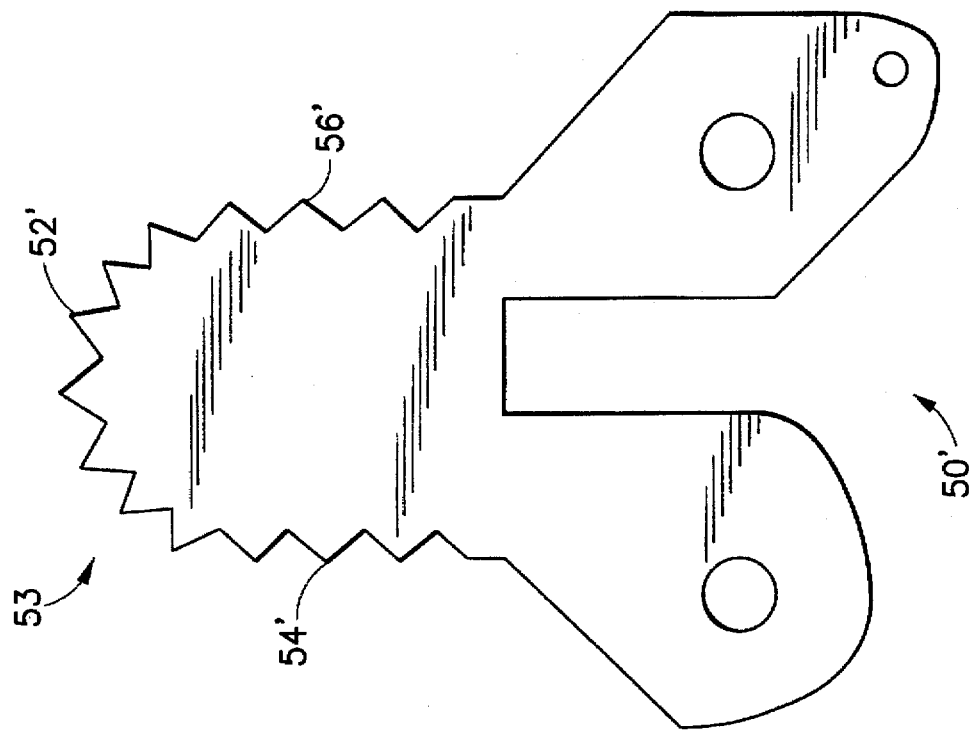
FIG. 6 is a view similar to FIG. 5 of a second embodiment of a forceps jaw according to the invention.

As shown in FIG. 6, a stamped sheet 50'(which is otherwise identical to the stamped sheet 50) may be provided with cut teeth 53 along the edges 52', 54', 56' to provide a jaw with a toothed cutting edge. Preferably, the teeth are offset by one half pitch to permit a pair of substantially identical jaws to mate hermaphroditically.

Figure 7:
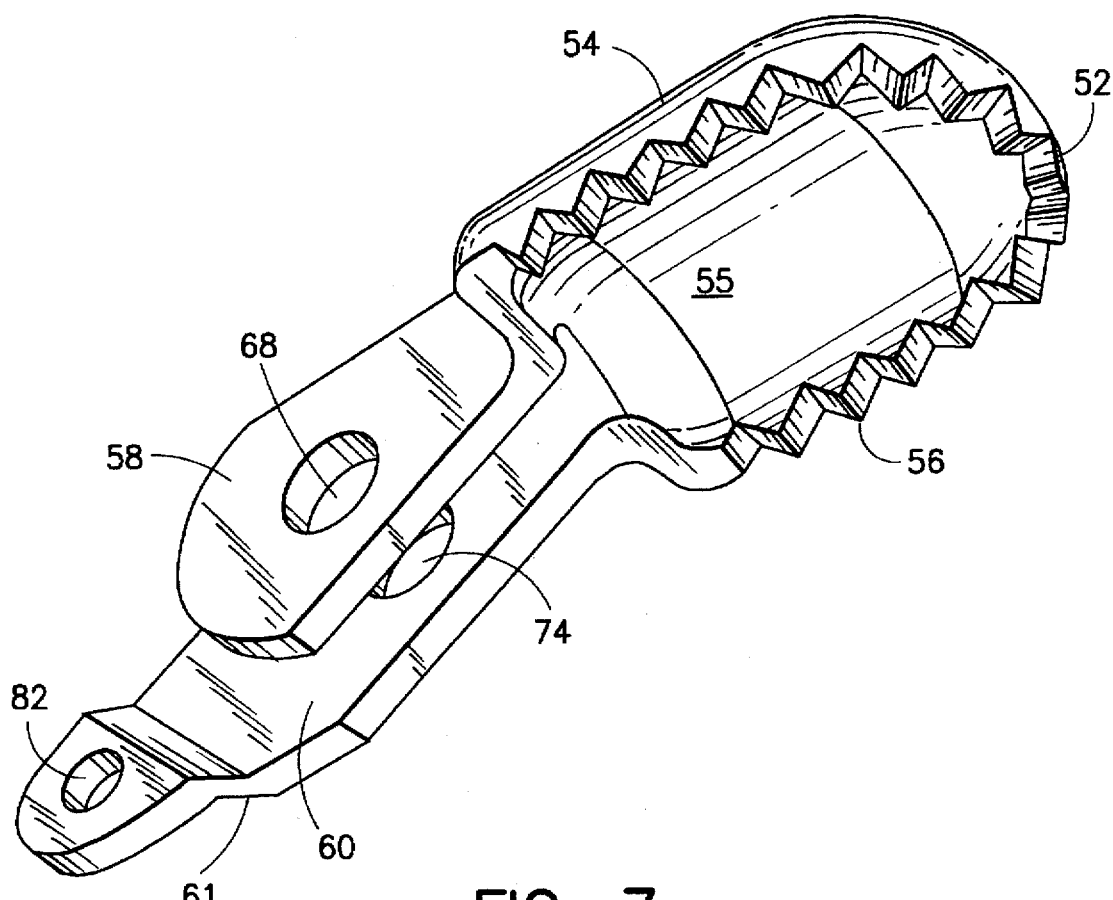

Turning now to FIGS. 7-9 and with reference to FIG. 5, the stamped sheet 50 (FIG. 5) is bent and progressively formed to form the forceps jaw 51. In particular, the sheet 50 is progressively formed in the area bounded by edges 52, 54, and 56 to create a jaw cup 55 and the lobes 58 and 60 are bent up substantially parallel to each other to form a pair of tangs. As seen in FIGS. 7-9, after the lobes 58, 60 are bent to a position where they are parallel to each other, the mounting holes 68, 74 are substantially coaxially aligned. In addition, as seen best in FIG. 7, the coupling hole 82 in the ear (tang) 60 is located proximal of the mounting holes 68, 74. Moreover, the coupling hole 82 is located in a levering position relative to the jaw cup 55 with reference to the mounting holes 68, 74. According to a presently preferred embodiment of the invention, a proximal portion of the lobe (tang) 60 which includes the coupling hole 82 is offset with a z-bend to accommodate the distal end of a control wire as described in more detail below.

From the foregoing, those skilled in the art will appreciate that the formed jaw 51 is similar in geometry to the prior art jaw 36 described above except for the provision of an extra tang (lobe) 58. The extra tang (lobe) provides added stability and strength to the jaw.

Figure 10:
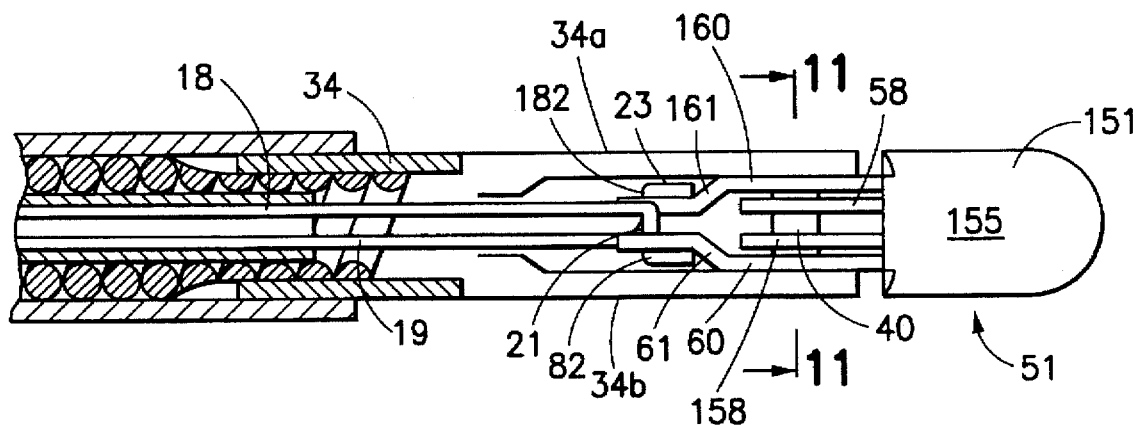
FIG. 10 is a view similar to prior art FIG. 3 showing a pair of jaws according to the invention mounted in a clevis.
Figure 11:
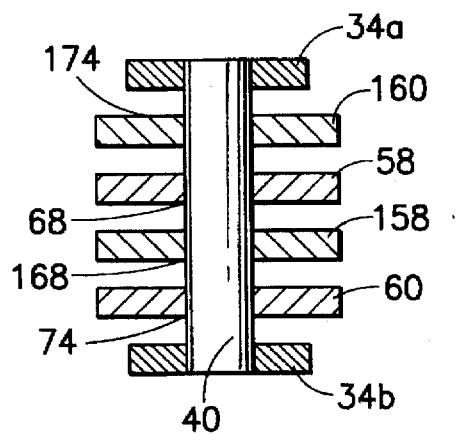
FIG. 11 is an enlarged cross sectional view taken along line 11—11 in FIG. 10.

Turning now to FIGS. 10 and 11, two forceps jaws 51 and 151 are mounted between the arms 34a, 34b of a clevis 34. The jaws 51 and 151 are substantially identical and similar reference numerals (incremented by 100) are used to refer portions of the jaw 151 which are substantially the same as portions of the jaw 51. The jaws 51 and 151 are mounted on a clevis axle 40 which passes through the holes 68 and 74 in the tangs 58 and 60 of the jaw 51 as well as through the holes 168 and 174 in the tangs 158 and 160 of the jaw 151. The tangs of the jaws are interleaved prior to mounting on the axle 40. Thus, the short tang 58 of the jaw 51 resides between the two tangs 158 and 160 of the jaw 151. Similarly, the short tang 158 of the jaw 151 resides between the two tangs 58 and 60 of the jaw 51. The long tangs 160 and 60 of the respective jaws are thus spaced apart from each other and located adjacent to respective clevis arms 34a, 34b. As seen best in FIG. 10, the proximal end of each long tang 160, 60 is provided with an inward z-bend 161, 61 near their respective coupling holes 182, 82. The z-bends in the tangs provide room for the distal ends of the control wires 18, 19 which are provided with corresponding z-bends 21, 23 where they pass through the coupling holes 182, 82

Figure 12:
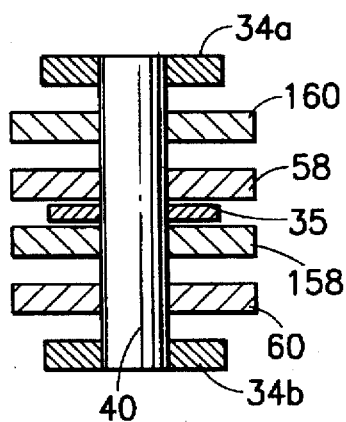
FIG. 12 is a view similar to FIG. 11 with a knife located between the jaw cups.

As mentioned above, the tangs of the forceps jaw of the invention are spaced apart a sufficient distance to allow the use of a flat knife between a pair of jaws. FIG. 12 illustrates an arrangement where a knife or spike 35 may be located between the short tangs 58, 158 of the jaws 51, 151 described above.

There have been described and illustrated herein a stamped biopsy forceps jaw and a method of making it. While particular embodiments of the invention have been described, it is not intended that the invention be limited thereto, as it is intended that the invention be as broad in scope as the art will allow and that the specification be read likewise. Thus, while particular materials such as stainless steel have been disclosed, it will be appreciated that other materials could be utilized. For example, the jaw could be made from a heat treatable metal. Also, while jaws with two tangs have been shown, it will be recognized that the method of the invention could be used to obtain a jaw with a single tang. Moreover, while particular configurations have been disclosed in reference to the shape of the jaw cup and the shape of the tangs, it will be appreciated that other configurations could be used as well. In fact, the method of the invention, and/or the double tang arrangement can be used in conjunction with different types of end effectors such as clamps, scissors, dissectors, etc. Furthermore, while the forceps jaw has been disclosed as having a tang with a z-bend, it will be understood that different configurations of the tang at the coupling hole can achieve the same or similar function as disclosed herein. It will therefore be appreciated by those skilled in the art that yet other modifications could be made to the provided invention without deviating from its spirit and scope as so claimed.

I claim:

1. A method of making a biopsy forceps jaw, comprising:
   a) obtaining a sheet of metallic material;
   b) cutting said sheet to form a pattern having a distal rounded edge and at least a first proximal lobe;
   c) cutting a first mounting hole in said first proximal lobe;
   d) forming said sheet to form a cup with said distal rounded edge forming a cutting edge; and
   e) bending said first proximal lobe to form a first tang.

2. A method according to claim 1, further comprising:
   f) cutting said sheet to form said pattern with a second proximal lobe;
   g) cutting a second mounting hole in said second proximal lobe; and
   h) bending said second proximal lobe to form a second tang substantially parallel to said first tang.

3. A method according to claim 2, wherein:
   said first proximal lobe is longer than said second proximal lobe.

4. A method according to claim 3, further comprising:
   i) cutting a coupling hole in a proximal portion of said first proximal lobe.

5. A method according to claim 4, further comprising:
   j) bending said first proximal lobe to form a z-bend between said coupling hole and said first mounting hole.

6. A method according to claim 1, wherein:
   said sheet is stainless steel.

7. A method according to claim 1, wherein:
   said cutting operations are performed by stamping.

8. A method according to claim 1, wherein:
   said step of cutting said sheet to form a pattern having a distal rounded edge and at least a first proximal lobe includes forming a plurality of teeth along said distal rounded edge.

9. A method according to claim 8, wherein:
   said step of forming a plurality of teeth includes arranging said teeth to be offset by one half pitch so that said biopsy forceps jaw is hermaphroditic.

10. A biopsy forceps jaw, comprising:
    a) a distal jaw cup having a cutting edge; and
    b) at least a first proximal tang extending proximally from said distal jaw cup and having a first mounting hole, wherein said biopsy forceps jaw is formed by,
       i) obtaining a sheet of metallic material;
       ii) cutting said sheet to form a pattern having a distal rounded edge and at least a first proximal lobe;
       iii) cutting said first mounting hole in said first proximal lobe;
       iv) forming said sheet to form said cup with said distal rounded edge forming said cutting edge; and
       v) bending said first proximal lobe to form said first proximal tang.

11. A biopsy forceps jaw, according to claim 10, further comprising:
    c) a second proximal tang extending proximally from said distal jaw cup and substantially parallel to said first proximal tang, said second proximal tang having a second mounting hole, wherein said biopsy forceps jaw is further formed by,
       vi) cutting said sheet to form said pattern with a second proximal lobe;
       vii) cutting said second mounting hole in said second proximal lobe; and
       viii) bending said second proximal lobe to form said second tang.

12. A biopsy forceps jaw according to claim 11, wherein:
    said first tang is longer than said second tang.

13. A biopsy forceps jaw according to claim 12, wherein:
    said first tang has a coupling hole, and said biopsy forceps jaw is further formed by,
       ix) cutting said coupling hole in a proximal portion of said first proximal lobe.

14. A biopsy forceps jaw according to claim 13, wherein:
    said first tang has a z-bend between said first mounting hole and said coupling hole, and said biopsy forceps jaw is further formed by,
       x) bending said first proximal lobe to form said z-bend between said coupling hole and said first mounting hole.

15. A method according to claim 10, wherein:
    said sheet is stainless steel.

16. A biopsy forceps law according to claim 10, wherein:
    said cutting operations are performed by stamping.

17. An endoscopic end effector, comprising:
    a distal working end and a pair of substantially parallel tangs extending proximally from said distal working end, at least one of said tangs defining a mounting hole for mounting said end effector on a clevis and at least one of said tangs defining a coupling hole for coupling said end effector to a control member, wherein a first one of said pair of tangs is shorter than a second one of said pair of tangs.

18. An endoscopic end effector according to claim 17, wherein:
    both of said pair of tangs define mounting holes and said second one of said pair of tangs defines said coupling hole.

19. An endoscopic instrument, comprising:
    a) a hollow tube having a proximal end and a distal end;
    b) a control member extending through said hollow tube and having a proximal end and a distal end;
    c) actuation means coupled to said proximal end of said hollow tube and said proximal end of said control member for effecting longitudinal displacement of said control member relative to said hollow tube;
    d) a clevis means coupled to said distal end of said hollow tube;
    e) a first end effector having a distal working end and first and second substantially parallel tangs extending proximally from said distal working end, at least one of said tangs defining a mounting hole for mounting said end effector on said clevis means and at least one of said tangs defining a coupling hole for coupling said end effector to said control member; and f) a second end effector having a distal working end and first and second substantially parallel tangs extending proximally from said distal working end, at least one of said tangs defining a mounting hole for mounting said end effector on said clevis means and at least one of said tangs defining a coupling hole for coupling said end effector to said control member, wherein said first tang of said first end effector is shorter than said second tang of said first end effector, and said first tang of said second end effector is shorter than said second tang of said second end effector.

20. An endoscopic instrument according to claim 19, wherein:

said tangs of said first end effector are interleaved with said tangs of said second end effector such that said first tang of said first end effector resides between said first and second tangs of said second end effector and said first tang of said second end effector resides between said first and second tangs of said first end effector.

* * * * *